US009469662B2

(12) United States Patent
Jaekel et al.

(10) Patent No.: US 9,469,662 B2
(45) Date of Patent: Oct. 18, 2016

(54) PROCESS FOR PREPARING OPTICALLY ACTIVE BIOPHOSPHINYLALKANES

(75) Inventors: Christoph Jaekel, Limburgerhof (DE); Rocco Paciello, Bad Duerkheim (DE)

(73) Assignee: BASF SE (DE)

( * ) Notice: Subject to any disclaimer, the term of this patent is extended or adjusted under 35 U.S.C. 154(b) by 696 days.

(21) Appl. No.: 11/997,027

(22) PCT Filed: Jul. 26, 2006

(86) PCT No.: PCT/EP2006/064709
§ 371 (c)(1),
(2), (4) Date: Jan. 28, 2008

(87) PCT Pub. No.: WO2007/012655
PCT Pub. Date: Feb. 1, 2007

(65) Prior Publication Data
US 2008/0242893 A1 Oct. 2, 2008

(30) Foreign Application Priority Data

Jul. 29, 2005 (DE) ........................ 10 2005 036 340

(51) Int. Cl.
*C07F 9/50* (2006.01)
(52) U.S. Cl.
CPC ............ *C07F 9/5027* (2013.01); *Y02P 20/582* (2015.11)
(58) Field of Classification Search
CPC .................................................. C07F 9/5027
USPC .................................................. 568/14, 395
See application file for complete search history.

(56) References Cited

U.S. PATENT DOCUMENTS

| 4,237,072 A | 12/1980 | Aviron-Violet et al. |
| 5,801,287 A | 9/1998 | Regnat et al. |
| 5,847,200 A | 12/1998 | Bahrmann et al. |

FOREIGN PATENT DOCUMENTS

| DE | 19609336 C1 | 3/1997 |
| DE | 10033956 A1 | 3/2001 |
| EP | 0111950 A2 | 6/1984 |
| EP | 0807636 A1 | 11/1997 |
| EP | 1182205 | * 2/2002 |
| EP | 1182205 A1 | 2/2002 |
| JP | 54-014911 | 2/1979 |

OTHER PUBLICATIONS

Matteoli et al., {Synthesis of the chiral diphosphine ligand 2,3bis(diphenylphosphino)butane (Chiraphos), Tetrahedon: Asymmetry, vol. 8, No. 9, 1997, pp. 1403-1409}.*
Han et al., {Nickel-catalyzed addition of P(O)-H bonds to propargyl alcohols: one-pot generation of phosphinoyl 1,3-butadienes, Organic Letters (2005), 7(14), 2909-2911.*
Fryzuk et al., {Asymmetric Synthesis. Production of Optically Active Amino Acids by Catalytic Hydrogenation, Journal of the American Chemical Society 99:19, 1977}.*
Tsvetkov, et al. A simple synthesis and some synthetic applications of substituted phosphide and phosphinite anions, Synthesis, 3, 198-208, 1986.*
Yamashita, et al., "Nucleophilic Substitution with Phosphide Anions Prepared by an Action of Sodium Dihydridobis (2-methoxyethanolato) aluminate on Phosphorus Compounds," Bull. Chem. Soc. Jpn., 56, 219-222, 1983.*
Von Ludwig Maier, "48. Organische Phosphorverbindungen XXXI. Ein einfaches Verfahren zur Herstellung von Alkylen-bzw. Arylen-diphosphiniten und von Bis-(dialkyl- und diaryl-phosphinyl)-alkanen [1]", *Schweizerische chemische Gesellschaft, Basel*, pp. 405-413 (1968). (abstract only).
Wife et al., "Phosphine Oxide Anions in the Synthesis of Phosphine Ligands", *Synthesis*, pp. 71-73 (1983).
Matteoli et al., "Synthesis of the chiral diphosphine ligand 2,3-bis(diphenylphosphino)butane (CHIRAPHOS)", *Tetrahedron: Asymmetry*, vol. 8, No. 9, pp. 1403-1409 (1997).
Chapuis et al., "Synthesis of Citronellal by $Rh^I$-Catalysed Asymmetric Isomerization of N,N-Diethyl-Substituted Geranyl- and Nerylamines or Geraniol and Nerol in the Presence of Chiral Diphosphino Ligands, under Homogeneous and Supported Conditions", *Helvetica Chimica Acta*, vol. 84, pp. 230-242 (2001).
K. Yamamoto et al., "Optimization of asymmetric hydrogeneration of 3-phenyl-3-butenoic acid catalyzed by rhodium(I)-4,5-bis[(diphenylphosphino)methyl]-2,2-dimethyldioxolane (DIOP)", Journal of Organometallic Chemistry, vol. 370, pp. 319-332, 1989.

* cited by examiner

*Primary Examiner* — Paul A Zucker
*Assistant Examiner* — Mark Luderer
(74) *Attorney, Agent, or Firm* — Drinker Biddle & Reath LLP

(57) ABSTRACT

The present invention relates to a process for preparing optically active bisphosphinylalkanes from the correspondingly substituted, racemic 1,2-diols. The optically active bisphosphinylalkanes which can be obtained in this way are suitable as ligands for preparing chiral transition metal catalysts.

18 Claims, No Drawings

PROCESS FOR PREPARING OPTICALLY ACTIVE BIOPHOSPHINYLALKANES

RELATED APPLICATIONS

This application is a national stage application (under 35 U.S.C. §371) of PCT/EP2006/064709, filed Jul. 26, 2006, which claims benefit of German application 10 2005 036 340.7, filed Jul. 29, 2005.

TECHNICAL FIELD OF THE INVENTION

The present invention relates to a process for preparing optically active bisphosphinylalkanes from the correspondingly substituted, racemic 1,2-diols. The optically active bisphosphinylalkanes which can be obtained in this way are suitable as ligands for preparing chiral transition metal catalysts.

The use of chiral bisphosphinylalkanes for preparing chiral transition metal catalysts is well known. As for many applications of particularly high-performance catalysts, the combination of an Rh complex with a chiral bisphosphane such as (R,R)-2,3-bisdiphenylphosphinobutane ("(R,R)-chiraphos") has been found to be useful. This ligand and processes for preparing it were described as early as 1977 (Bosnich et al. J. Am. Chem. Soc. 1977, 99, 6262-6267). Over the years, further methods of preparing this ligand have been described (Jansen et al. Tetrahedron: Asymmetry 1990, 1, 719-720; Matteoli et al. Tetrahedron: Asymmetry 1997, 8, 1403-1410), Methods of preparing similar ligands have likewise been described (Chem. Ber. 1986, 119, 3326; Tetrahedron: Asymmetry 1990, 1, 895-912; Chem. Pharm. Bull. 1990, 38, 818; Synthesis 1992, 951; J. Organomet. Chem. 1998, 560, 257; EP1182205).

The methods/processes described hitherto for preparing (R,R)-chiraphos and its analogues are not suitable for economically advantageous implementation on an industrial scale.

PRIOR ART

DE-A 100 33 956 discloses a process for preparing symmetrical and unsymmetrical bisphosphino compounds by reacting a cyclic alkylene sulfate with a phosphorus(III)-alkali metal compound.

In J. Chem. Soc., Chem. Comm., 1983, 805-805, R. L. Wife et al. describe the synthesis of 1,2-ethylenebis(diarylphosphine oxides) by reaction of diarylphosphine oxide anions with suitable oxiranes. Here, sequential ring opening and substitution take place.

The corresponding process carried out in a polar aprotic solvent and in the presence of a basic compound capable of forming a phosphinoyl anion is disclosed in EP-A 0 111 950.

EP-A 0 807 636 discloses specific diphosphines which are in the form of ammonium carboxylates, sulfonates or phosphonates having a singly or multiply charged diphosphine anion and the corresponding number of ammonium cations as counterions. In addition, a process for preparing these compounds, in which diphlenylphosphine oxide is reacted with an appropriate dihalide in the presence of a base, is disclosed.

DE 196 09 336 relates to specific bis(diarylphoshines) which bear amine-substituted aryl radicals and can be present in cationic form with a counterion and also a process for preparing them, in which the individual phosphane ligands are joined in succession by substitution with a suitable dihalide.

OBJECT OF THE INVENTION

It was an object of the present invention to provide a process for preparing optically active vicinal bisphosphinylalkanes which can be carried out in high yields by means of a small total number of steps starting from inexpensive, readily available starting materials and is suitable for reactions on an industrial scale.

DESCRIPTION OF THE INVENTION AND THE PREFERRED EMBODIMENTS

According to the invention, this object has been achieved by the provision of a process for preparing optically active bisphosphinylalkanes of the formula (I)

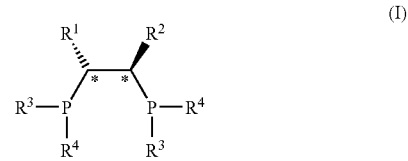

where the radicals $R^1$ and $P^2$ can be identical or different and are each a straight-chain, branched or cyclic alkyl radical which has from 1 to 12 carbon atoms and may bear one or more identical or different substituents selected from the group consisting of the substituents halogen, $C_6$-$C_{12}$-aryl, $NR^5R^6$, $NHR^7$ and $OR^8$ or an aryl radical which has from 6 to 12 carbon atoms and may bear one or more identical or different substituents selected from the group consisting of the substituents $C_1$-$C_{12}$-alkyl, halogen, $C_6$-$C_{12}$-aryl, $NR^{5'}R^{6'}$, $NHR^{7'}$ and $OR^{8'}$ or together form an aliphatic ring or bicycle which has from 4 to 12 ring members and may bear one or more substituents selected from the group consisting of the substituents halogen, oxo, $C_6$-$C_{12}$-aryl, $C_1$-$C_{10}$-acyl and $C_1$-$C_{10}$-sulfonyl and may comprise one or more heteroatoms O or $NR^9$, and $R^3$ and $R^4$ can be identical or different and are each a straight-chain, branched or cyclic alkyl radical having from 1 to 12 carbon atoms or an aryl radical having from 6 to 12 carbon atoms, each of which may bear one or more identical or different substituents selected from the group consisting of the substituents $C_1$-$C_{12}$-alkyl, halogen, $NR^{5''}R^{6''}$, $NHR^{7''}$, $OR^{8''}$, sulfonyl and $NR^{10}R^{11}R^{12}R^{13}$, $C(O)OR^{14}$, $C(O)NR^{14'}R^{14''}$ and the radicals $R^5$, $R^6$ to $R^{5'''}$, $R^{6'''}$ are each, independently of one another, $C_1$-$C_{12}$-alkyl or $C_6$-$C_{12}$-aryl, $R^7$ to $R^{7'''}$ are each $C_1$-$C_{10}$-acyl or $C_1$-$C_{10}$-sulfonyl, $R^8$ to $R^{8'''}$ are each $C_1$-$C_{12}$-alkyl or $C_6$-$C_{12}$-aryl, $R^9$ is $C_1$-$C_{12}$-alkyl, $C_6$-$C_{12}$-aryl, $C_1$-$C_{10}$-acyl or $C_1$-$C_{10}$-sulfonyl, $R^{10}$ to $R^{13}$ are each, independently of one another, $C_1$-$C_{12}$-alkyl, $C_6$-$C_{12}$-aryl or $C_7$-$C_{17}$-aralkyl, $R^{14}$, $R^{14'}$ are each hydrogen, $C_1$-$C_{12}$-alkyl, $C_6$-$C_{12}$-aryl or $C_7$-$C_{17}$-aralkyl, $R^{14''}$ is $C_1$-$C_{12}$-alkyl, $C_6$-$C_{12}$-aryl or $C_7$-$C_{17}$-aralkyl, and

* denotes an asymmetrically substituted carbon atom, which comprises the reaction steps a) to d):
a) reaction of a diol of the formula (II)

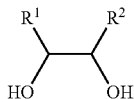
(II)

where the radicals $R^1$ and $R^2$ have the same meanings as in the formula (I),
to form a compound of the formula (III)

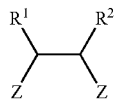
(III)

where the radicals $R^1$ and $R^2$ have the same meanings as in the formula (I), and the radicals
Z are each a leaving group or together form a structural fragment selected from the group consisting of the structural fragments —O—S(O)$_2$—O—, —O—P(O)—(OR$^{15}$)$_2$—O—, —O—C(O)—O— and —O—C(O)—C(O)—O—, where $R^{15}$ can be $C_1$-$C_{12}$-alkyl, $C_7$-$C_{17}$-aralkyl or $C_6$-$C_{12}$-aryl,
b) reaction of the compound of the formula (III) obtained in step a) with a phosphate of the formula (IV)

(IV)

where the radicals $R^3$ and $R^4$ have the same meanings as in the formula (I),
in the presence of a base which is capable of deprotonating the phosphite of the formula (IV) used,
to form a racemic 1,2-trans-configured diphosphite of the formula (V)

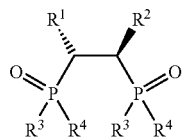
(V)

where the radicals $R^1$ to $R^4$ have the same meanings as in the formula (I),
c) resolution of the racemic diphosphite of the formula (V) obtained in step b) to give an optically active diphosphite of the formula (V*)

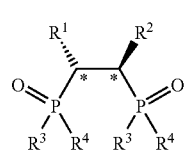
(V*)

where the radicals $R^1$ to $R^4$ have the same meanings as in the formula (I), and
* denotes an asymmetrically substituted carbon atom, and
d) reduction of the compound of the formula (V*) obtained in step c) to give the compound of the formula (I).

The process of the invention is suitable for preparing optically active bisphosphinylalkanes of the formula (I) in which the radicals $R^1$ to $R^4$ and the substituents $R^5$ to $R^{15}$ have the abovementioned meanings. The number of carbon atoms mentioned for each of the radicals $R^1$ to $R^4$ does not comprise that of the substituents attached to the radicals in each case. The following meanings of the substituents mentioned may be given by way of example:

$C_1$-$C_6$-Alkyl is, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl.

$C_1$-$C_{12}$-Alkyl is, for example, the abovementioned $C_1$-$C_6$-alkyl and also heptyl, 2-methylhexyl, 3-methylhexyl, 3-ethylhexyl, 2,2-dimethylpentyl, 3,3-dimethylpentyl, 2,3-dimethylpentyl, 2,4-dimethylpentyl, 2,2,3-trimethylbutyl, octyl, 2-methylheptyl, 3-methylheptyl, 4-methylheptyl, 3-ethylhexyl, 4-ethylhexyl, 2,2-dimethylhexyl, 3,3-dimethylhexyl, 2,3-dimethylhexyl, 2,4-dimethylhexyl, 2,5-dimethylhexyl, 3,4-dimethylhexyl, 3,5-dimethylhexyl, 2,3,4-trimethylpentyl, 2,2,3-trimethylpentyl, 2,2,4-trimethylpentyl, 2,3,3-trimethylpentyl, 3-ethyl-2-methylpentyl, 3-ethyl-3-methylpentyl, 2,2,3,3-tetramethylbutyl, nonyl, 2-methyloctyl, 3-methyloctyl, 4-methyloctyl, 3-ethylheptyl, 4-ethylheptyl, 2,2-dimethylheptyl, 3,3-dimethylheptyl, 4,4-dimethylheptyl, 2,3-dimethylheptyl, 2,4-dimethylheptyl, 2,5-dimethylheptyl, 2,6-dimethylheptyl, 3,4-dimethylheptyl, 3,5-dimethylheptyl, 3,6-dimethylheptyl, 2,3,4-trimethylhexyl, 2,2,3-trimethylhexyl, 2,2,4-trimethylhexyl, 2,2,5-trimethylhexyl, 2,3,3-trimethylhexyl, 3,3,4-trimethylhexyl, 3,3,5-trimethylhexyl, 3-ethyl-2-methylhexyl, 3-ethyl-3-methylhexyl, 3-ethyl-4-methylhexyl, 3-ethyl-5-methylhexyl, 2,2,3,3-tetramethylpentyl, 2,2,4,4-tetramethylpentyl, 2,2,3,4-tetramethylpentyl, 2,3,3,4-tetramethylpentyl, 3,3-tetraethylpentyl, decyl, 2-methylnonyl, 3-methylnonyl, 4-methylnonyl, 5-methylnonyl, 3-ethyloctyl, 4-ethyloctyl, 5-ethyloctyl, 2,2-dimethyloctyl, 3,3-dimethyloctyl, 4,4-dimethyloctyl, 5,5-dimethyloctyl, 2,3-dimethyloctyl, 2,4-dimethyloctyl, 2,5-dimethyloctyl, 2,6-dimethyloctyl, 2,7-dimethyloctyl, 3,4-dimethyloctyl, 3,5-dimethyloctyl, 3,6-dimethyloctyl, 4,5-dimethyloctyl, 2,3,4-trimethylheptyl, 2,2,3-trimethylheptyl, 2,2,4-trimethylheptyl, 2,2,5-trimethylheptyl, 2,3,3-trimethylheptyl, 3,3,4-trimethylheptyl, 3,3,5-trimethylheptyl, 3-ethyl-2-methylheptyl, 3-ethyl-3-methylheptyl, 3-ethyl-4-methylheptyl, 3-ethyl-5-methylheptyl, 2,2,3,3-tetramethylhexyl, 2,2,4,4-tetramethylhexyl, 2,2,3,4-tetramethylhexyl, 2,3,3,4-tetramethylhexyl, 3,3-tetraethylhexyl, undecyl, 2-methyldecyl, 3-methyldecyl, 4-methyldecyl, 5-methyldecyl, 3-ethylnonyl, 4-ethylnonyl, 5-ethylnonyl, 2,2-dimethylnonyl, 3,3-dimethylnonyl, 4,4-dimethylnonyl, 5,5-dimethylnonyl, 2,3-dimethylnonyl, 2,4-dimethylnonyl, 2,5-dimethylnonyl, 2,6-dimethylnonyl, 2,7-dimethylnonyl, 3,4-dimethylnonyl, 3,5-dimethylnonyl, 3,6-dimethylnonyl, 4,5-dimethylnonyl, 2,3,4-trimethyloctyl, 2,2,3-trimethyloctyl, 2,2,4-trimethyloctyl, 2,2,5-trimethyloctyl, 2,3,3-trimethyloctyl, 3,3,4-trimethyloctyl, 3,3,5-trimethyloctyl, 3-ethyl-2-methyloctyl, 3-ethyl-3-methyloctyl, 3-ethyl-4-methyloctyl, 3-ethyl-5-methyloctyl, 2,2,3,3-tetramethylheptyl, 2,2,4,4-tetramethylheptyl, 2,2,3,4-tetramethylheptyl, 2,3,3,4-tetramethylheptyl, 3,3-tetraethylheptyl, dodecyl, 2-methylundecyl, 3-methylundecyl, 4-methylundecyl, 5-methylundecyl, 3-ethyldecyl, 4-ethyldecyl, 5-ethyldecyl, 2,2-dimethyldecyl, 3,3-dimethyldecyl, 4,4-dimethyldecyl, 5,5-dimethyldecyl, 2,3-dimethyldecyl, 2,4-dimethyldecyl, 2,5-dimethyldecyl, 2,6-dimethyldecyl, 2,7-dimethyldecyl, 3,4-dimethyldecyl, 3,5-dimethyldecyl, 3,6-dimethyldecyl, 4,5-dimethyldecyl, 2,3,4-trimethylnonyl, 2,2,3-trimethylnonyl, 2,2,4-trimethylnonyl, 2,2,5-trimethylnonyl, 2,3,3-trimethylnonyl, 3,3,4-trimethylnonyl, 3,3,5-trimethylnonyl, 3-ethyl-2-methylnonyl, 3-ethyl-3-methylnonyl, 3-ethyl-4-methylnonyl, 3-ethyl-5-methylnonyl, 2,2,3,3-tetramethyloctyl, 2,2,4,4-tetramethyloctyl, 2,2,3,4-tetramethyloctyl, 2,3,3,4-tetramethyloctyl, 3,3-tetraethyloctyl.

In addition, for the purposes of the present invention, halogen is fluorine, chlorine, bromine or iodine, preferably chlorine, bromine or iodine.

$C_6$-$C_{12}$-Aryl is, for example, phenyl, 1-methylphenyl, 2-methylphenyl, 3-methylphenyl, 1-ethylphenyl, 2-ethylphenyl, 3-ethylphenyl, 1-propylphenyl, 2-propylphenyl, 3-propylphenyl, 1-isopropylphenyl, 2-isopropylphenyl, 3-isopropylphenyl, 1-butylphenyl, 2-butylphenyl, 3-butylphenyl, 1-isobutylphenyl, 2-isobutylphenyl, 3-isobutylphenyl, 1-sec-butylphenyl, 2-sec-butylphenyl, 3-sec-butylphenyl, 1-tert-butylphenyl, 2-tert-butylphenyl, 3-tert-butylphenyl, 1-(1-pentenyl)phenyl, 2-(1-pentenyl)phenyl, 3-(1-pentenyl)phenyl, 1-(2-pentenyl)phenyl, 2-(2-pentenyl)phenyl, 3-(2-pentenyl)phenyl, 1-(3-pentenyl)phenyl, 2-(3-pentenyl)phenyl, 3-(3-pentenyl)phenyl, 1-(1-(2-methylbutyl))phenyl, 2-(1-(2-methylbutyl))phenyl, 3-(1-(2-methylbutyl))phenyl, 1-(2-(2-methylbutyl))phenyl, 2-(2-(2-methylbutyl))phenyl, 3-(2-(2-methylbutyl))phenyl, 1-(3-(2-methylbutyl))phenyl, 2-(3-(2-methylbutyl))phenyl, 3-(3-(2-methylbutyl))phenyl, 1-(4-(2-methylbutyl))phenyl, 2-(4-(2-methylbutyl))phenyl, 3-(4-(2-methylbutyl))phenyl, 1-(1-(2,2-dimethylpropyl))phenyl, 2-(1-(2,2-dimethylpropyl))phenyl, 3-(1-(2,2-dimethylpropyl))phenyl, 1-(1-hexenyl)phenyl, 2-(1-hexenyl)phenyl, 3-(1-hexenyl)phenyl, 1-(2-hexenyl)phenyl, 2-(2-hexenyl)phenyl, 3-(2-hexenyl)phenyl, 1-(3-hexenyl)phenyl, 2-(3-hexenyl)phenyl, 3-(3-hexenyl)phenyl, 1-(1-(2-methylpentenyl))phenyl, 2-(1-(2-methylpentenyl))phenyl, 3-(1-(2-methylpentenyl))phenyl, 1-(2-(2-methylpentenyl))phenyl, 2-(2-(2-methylpentenyl))phenyl, 3-(2-(2-methylpentenyl))phenyl, 1-(3-(2-methylpentenyl))phenyl, 2-(3-(2-methylpentenyl))phenyl, 3-(3-(2-methylpentenyl))phenyl, 1-(4-(2-methylpentenyl))phenyl, 2-(4-(2-methylpentenyl))phenyl, 3-(4-(2-methylpentenyl))phenyl, 1-(5-(2-methylpentenyl))phenyl, 2-(5-(2-methylpentenyl))phenyl, 3-(5-(2-methylpentenyl))phenyl, 1-(1-(2,2-dimethylbutenyl))phenyl, 2-(1-(2,2-dimethylbutenyl))phenyl, 3-(1-(2,2-dimethylbutenyl))phenyl, 1-(3-(2,2-dimethylbutenyl))phenyl, 2-(3-(2,2-dimethylbutenyl))phenyl, 3-(3-(2,2-dimethylbutenyl))phenyl, 1-(4-(2,2-dimethylbutenyl))phenyl, 2-(4-(2,2-dimethylbutenyl))phenyl, 3-(4-(2,2-dimethylbutenyl))phenyl or naphthyl.

$C_1$-$C_{10}$-Acyl is a straight-chain, branched or cyclic acyl radical having from 1 to 10 carbon atoms, for example: formyl, acetyl, propionyl, butanoyl, pentanoyl, hexanoyl, heptanoyl, octanoyl, nonanoyl, decanoyl, pivaloyl, 1-cyclohexylformyl, phthaloyl, alkyloxycarbonyl, e.g. methyloxycarbonyl, ethyloxycarbonyl, propyloxycarbonyl, butyloxycarbonyl, pentyloxycarbonyl, hexyloxycarbonyl, heptyloxycarbonyl, octyloxycarbonyl, nonyloxycarbonyl, tert-butyloxycarbonyl, benzyloxycarbonyl or alkylamidocarbonyl, e.g. N,N-dimethylamidocarbonyl.

For the purposes of the present invention, $C_1$-$C_{10}$-sulfonyl is a sulfonyl radical having from 1 to 10 carbon atoms, for example methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, phenylsulfonyl, (3-bromo)phenylsulfonyl, (3-methyl)phenylsulfonyl or trifluoromethylsulfonyl.

For the purposes of the present invention, $C_7$-$C_{17}$-aralkyl is, for example, phenylmethyl, 1-phenylethyl, 2-phenylethyl, 1-phenylpropyl, 2-phenylpropyl, 3-phenylpropyl, 1-phenylbutyl, 2-phenylbutyl, 3-phenylbutyl, 4-phenylbutyl, 1-phenylpentyl, 2-phenylpentyl, 3-phenylpentyl, 4-phenylpentyl, 5-phenylpentyl, 6-phenylhexyl, 7-phenylheptyl, 8-phenyloctyl, 9-phenylnonyl, 10-phenyldecyl, 11-phenylundecyl, methyl(1-naphthyl), methyl(2-naphthyl), 2-ethyl(1-naphthyl), 2-ethyl(2-naphthyl), 3-propyl(1-naphthyl), 3-propyl(2-naphthyl), 4-butyl(1-naphthyl), 4-butyl(2-naphthyl), 5-pentyl(1-naphthyl), 5-pentyl(2-naphthyl), 6-hexyl(1-naphthyl), 6-hexyl(2-naphthyl), 7-heptyl(1-naphthyl), 7-heptyl(2-naphthyl), methyl(1-biphenyl), methyl(2-biphenyl), methyl(3-biphenyl), 2-ethyl(1-biphenyl), 2-ethyl(2-biphenyl), 2-ethyl(3-biphenyl), 3-propyl(1-biphenyl), 3-propyl(2-biphenyl), 3-propyl(3-biphenyl), 4-butyl(1-biphenyl), 4-butyl(2-biphenyl), 4-butyl(3-biphenyl), 5-pentyl(1-biphenyl), 5-pentyl(2-biphenyl), 5-pentyl(3-biphenyl), 6-hexyl(1-biphenyl), 6-hexyl(2-biphenyl), 6-hexyl(3-biphenyl), 7-heptyl(1-biphenyl), 7-heptyl(2-biphenyl), 7-heptyl(3-biphenyl) or methylanthracenyl.

The following preferred meanings of the substituents mentioned may be given by way of example:

$NR^5R^6$ is, for example, dimethylamino, diethylamino, dipropylamino, dibutylamino, diphenylamino, di(3-methoxyphenyl)amino, di(3-bromophenyl)amino, dibenzylamino, di(3-methoxyphenyl)amino, di(3'-bromophenylmethyl)amino or phthaloylamino, $NHR^7$ is, for example, acetylamino, propanoylamino, butanoylamino, pivaloylamino, tosyl or methanesulfonylamino, $OR^8$ is, for example, methoxy, ethoxy, isopropoxy, tert-butoxy or benzyloxy, $NR^9$ is, for example, phenylamino, acetylamino, methylsulfonylamino and toluenesulfonylamino and $NR^{10}R^{11}R^{12}R^{13}$ is, for example, tetramethylammonium, tetraethylammonium, benzyltrimethylammonium or benzyltriethylammonium.

The symbol (*) denotes an asymmetrically substituted carbon atom, i.e. a tetrahedral carbon atom having four different radicals which is predominantly present in one of its two possible mirror image forms.

The process of the invention is preferably suitable for preparing optically active bisphosphinylalkanes of the formula (I) in which the radicals $R^1$ and $R^2$ are identical or different, preferably identical, and are each a straight-chain, branched or cyclic alkyl radical having from 1 to 12, preferably from 1 to 6, carbon atoms and may together form an aliphatic ring or bicycle which has from 4 to 12 ring members and may bear one or more, generally from 1 to about 3, substituents selected from the group consisting of the substituents halogen, $C_6$-$C_{10}$-aryl, $C_1$-$C_{10}$-acyl and $C_1$-$C_{10}$-sulfonyl and may comprise one or more heteroatoms O or $NR^9$. The radicals $R^3$ and $R^4$ are preferably identical or different and are each an aryl radical which has from 6 to 10 carbon atoms and may in each case bear one or more, generally from 1 to about 3, identical or different substituents selected from the group consisting of the substituents $C_1$-$C_6$-alkyl, halogen, $NR^{5''}R^{6''}$, $NHR^{7''}$, $OR^{8''}$, sulfonyl and $NR^{10}R^{11}R^{12}R^{13}$, $C(O)OR^{14}$, $C(O)NR^{14'}R^{14''}$.

Process products of the general formula (I) which are particularly preferred according to the invention are ones in which the radicals $R^1$ and $R^2$ together form a cyclohexyl ring and the radicals $R^3$ and $R^4$ are each unsubstituted phenyl or phenyl which is substituted as described above. Preference is likewise given according to the invention to process products of the formula (I) in which the radicals $R^1$ and $R^2$ are each methyl and the radicals $R^3$ and $R^4$ are each unsubstituted phenyl or phenyl which is substituted as described above.

The following compounds of the formulae (1) to (7) may be given as examples of process products which are preferred according to the invention:

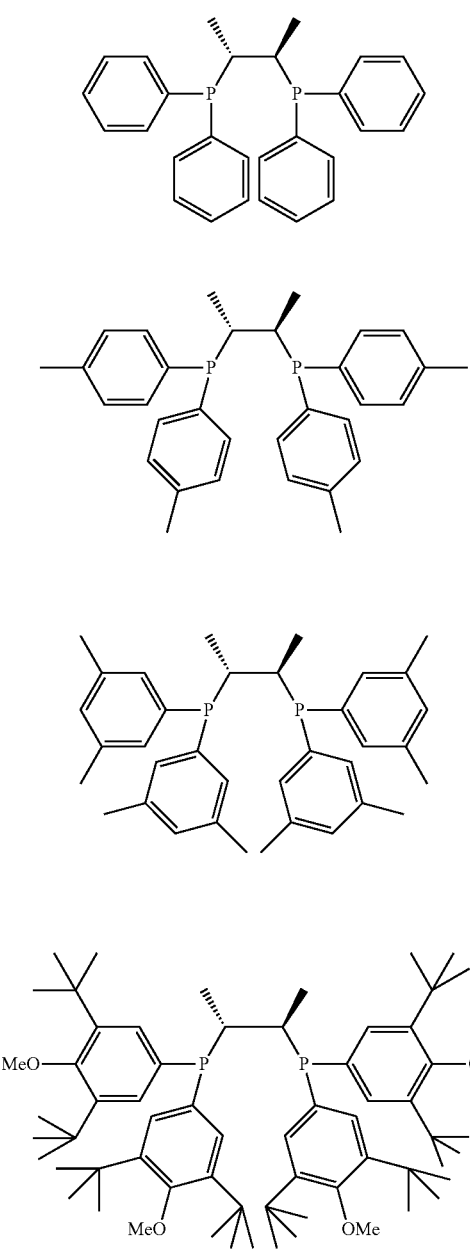

(1)
(2)
(3)
(4)

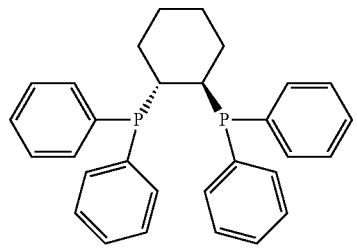

(5)

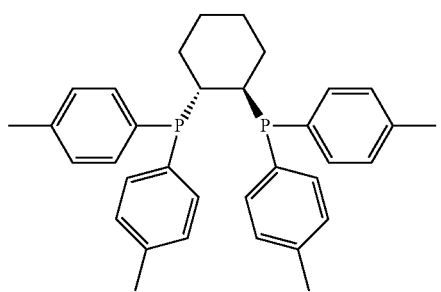

(6)

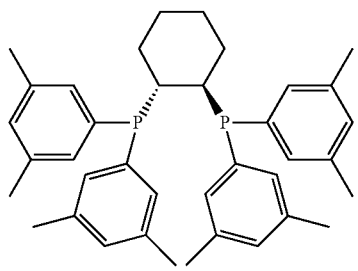

(7)

The abovementioned process products of the general formula (I) can, if desired, depending on the form of step c) of the process of the invention be prepared according to the invention in the form of their two enantiomers.

The process of the invention comprises the reaction steps a) to d), which are explained in more detail below:

In step a) of the process of the invention, a diol of the general formula (II) as starting compound

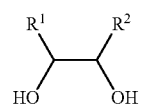

(II)

where the radicals $R^1$ and $R^2$ have the same meanings as in the desired process product of the general formula (I), is reacted to form a compound of the formula (III)

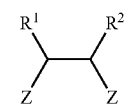

(III)

where the radicals $R^1$ and $R^2$ in the formula (III) have the same meanings as in the formula (II) and the radicals Z are each a leaving group or together form a structural fragment selected from the group consisting of the bridging structural fragments —O—S(O)$_2$—O—, —O—P(O)(OR$^{15}$)$_2$—O—, —O—C(O)—O— and —O—C(O)—C(O)—O—, where $R^{15}$ is $C_1$-$C_{12}$-alkyl, $C_7$-$C_{17}$-aralkyl or $C_6$-$C_{12}$-aryl.

For the purposes of the present invention, a leaving group is a structural element which can be replaced by attack of or reaction with nucleophiles.

Suitable starting compounds for preparing the compounds of the formula (III) are 1,2-diols of the formula (II) which can be used in the form of mixtures of the possible diastereomers but also, if desired, in the form of stereochemically uniform compounds. Preferred starting compounds of the formula (II) are, for example: 2,3-butanediol, 1,2-cyclohexanediol, 2,3-dihydroxydecalin, 3,4-dihydroxypyran, 3,4-dihydroxytetrahydrofuran, N-methyl-3,4-dihydroxypyrrolidine, N-benzyl-3,4-dihydroxypyrrolidine, N-acetyl-3,4-dihydroxypyrrolidine, N-pivaloyl-3,4-dihydroxypyrrolidine or 3,4-dihydroxythiophene.

The two hydroxy groups of the chosen starting compound of the formula (II) are converted into suitable leaving groups in step a) of the present invention. Suitable leaving groups are, for example: halide, preferably chloride, bromide or iodide, mesylate, tosylate, triflate, nonaflate, acetate, trifluoroacetate and benzoate. Leaving groups which are particularly preferred according to the invention in step a) are chloride, bromide, iodide, tosylate, mesylate and trifluoroacetate. Methods of converting the chosen starting compounds of the formula (II) into the compounds of the formula (III) are known per se to those skilled in the art and are described, for example, in J. Am. Chem. Soc. 1977, 99, 6262-6267 or Synthesis 1992, 951. In addition, activation of the hydroxyl groups for substitution in situ can also be carried out, for example, by complexation with a Lewis acid or use of conditions as are described by Mitsunobu, O. in Synthesis 1981, 1.

The two structural elements Z in the formula (III) can, in a further embodiment, together form a structural fragment selected from the group consisting of the structural fragments —O—S(O)$_2$—O—, —O—P(O)(OR$^{15}$)$_2$—O—, —O—C(O)—O— and —O—C(O)—C(O)—O—, where $R^{15}$ is $C_1$-$C_{12}$-alkyl, $C_7$-$C_{17}$-aralkyl or $C_6$-$C_{12}$-aryl. The compounds of the formula (III) are then cyclic sulfates, phosphates, carbonates or oxalates, with the phosphates mentioned being esterified by suitable groups as mentioned above, preferably by methyl, phenyl or benzyl. In a preferred embodiment of the process of the invention, a diol of the formula (II) is converted into a cyclic sulfate of the formula (VII).

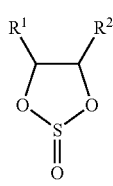

(VI)

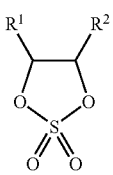

(VII)

This is advantageously effected by sulfonation of the diol of the formula (II) used, for example by the action of thionyl chloride to form the cyclic sulfite of the formula (VI) and subsequent oxidation by means of suitable oxidants such as KMnO$_4$ or TPAP (tetrapropylammonium perruthenate).

The intermediates of the general formula (III) which can be obtained according to step a) can be isolated in a customary manner and purified further if necessary. They serve as starting compounds for step b) of the process of the invention.

In step b) of the process of the invention, the compound of the formula (III) obtained in step a) is reacted with a phosphite of the formula (IV)

(IV)

where the radicals $R^3$ and $R^4$ have the meanings desired for the process product of the formula (I). The reaction is carried out in the presence of a base which is capable of deprotonating the phosphate of the formula (IV) used. In this way, step b) of the process gives a racemic, 1,2-trans-configured diphosphite of the formula (V)

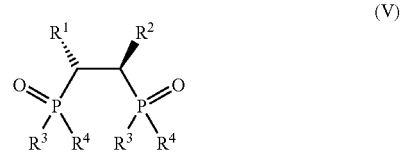

(V)

where the radicals $R^1$ to $R^4$ have the meanings desired for the process product of the formula (I) and corresponding to the compounds of the formulae (II) and (III) which have undergone step a).

In step b), the leaving groups or the cyclic leaving group Z are/is replaced by the nucleophile formed from the phosphite of the formula (IV) used and the base used by deprotonation. The reaction is preferably carried out in a dipolar aprotic solvent such as dimethyl sulfoxide, dimethylformamide, dimethylacetamide, N-methylpyrrolidinone, sulfolane or further solvents which appear suitable to a person skilled in the art in the presence of water. Suitable bases are, in particular, at least partially water-soluble bases such as alkali metal hydroxides (e.g. sodium hydroxide or potassium hydroxide), alkaline earth metal hydroxides (e.g. calcium hydroxide or magnesium hydroxide), alkali metal alkoxides (e.g. sodium or potassium methoxide or ethoxide) and alkaline earth metal alkoxides (e.g. calcium ethoxide or magnesium ethoxide). The bases mentioned are usually used in molar amounts of from about 1 to about 10 equivalents, based on the phosphite of the formula (IV) to be deprotonated, preferably in the form of aqueous solutions. The reaction is advantageously carried out at temperatures above about 0° C. Further substrate- or reagent-specific reaction conditions can be ascertained by means of routine experiments.

In this way, the desired 1,2 trans-configured diphosphites of the formula (V) are obtained in high yields and selectivities and can be isolated by methods known per se to those skilled in the art and purified further by, for example, crystallization. It has been found that the diphosphites of the general formula (V) prepared according to step b) of the present invention often have a higher diastereomeric purity than the corresponding precursor compounds of the formula (III) or (II) which are used, which indicates an isomerization following the two-fold substitution reaction, possibly by action of the base used. The diphosphites of the formula (V) prepared according to step b) are accordingly obtained in high diastereomeric purity in the form of racemic mixtures and are, according to the invention, treated further as described under step c).

In step c) of the present invention, resolution of the racemic diphosphite of the formula (V) obtained in step b) is carried out to give an optically active diphosphite of the formula (V*)

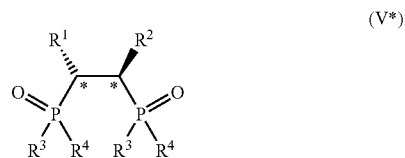

where the radicals $R^1$ to $R^4$ have the meanings desired for the process product of the formula (I) and corresponding to the compounds of the formulae (II), (III), (IV) and (V) which have undergone steps a) and b) and the symbol * denotes an asymmetrically substituted carbon atom.

Racemate resolutions of chiral diphosphites are known and are described, for example, in J. Org. Chem. 1986, 51, 629-635. The resolution of the racemic diphosphite of the formula (V) obtained in step b) is preferably carried out by adduct formation with suitable chiral auxiliary reagents such as chiral acids, for instance chiral carboxylic or sulfonic acids, in optically active form. Chiral acids suitable for this purpose are, for example, (+)- or (−)-dibenzoyl tartrate or (+)- or (−)-camphor sulfonic acid. In step c) of the process of the invention, preference is given to carrying out a crystallization of the racemates of the formula (V) obtained in step b) in the presence of the abovementioned enantiomerically pure auxiliary reagents, if appropriate at reduced temperatures. The diastereomeric adducts obtained in this way can then be isolated in a manner known to those skilled in the art. Dissociation of the diastereomeric adducts isolated in this way gives the free optically active diphosphites of the formula (V*) and the chiral auxiliary reagent used, which can be reused for further reactions.

The optically active diphosphites of the formula (V*) obtained in this way according to step c) of the process of the invention are finally reduced in step d) to give the desired optically active bisphosphinylalkane of the formula (I). Any undesired optically active isomer can, for example, be racemized in the presence of a base and reused in step c) of the process. Reductions of diphosphites to bisphosphinylalkanes are known and are described, for example, by Matteoli et al. in Tetrahedron: Asymmetry 1997, 8, 1403-1409, using trichlorosilane in boiling xylene. Suitable methods of reduction may be regarded as those in which racemization of the chiral diphosphite of the formula (V*) used in each case and the bisphosphinylalkane of the formula (I) formed does not occur or occurs only to a small extent. Further suitable reducing agents which can thus be used advantageously in step d) of the process of the invention are, for example: lithium aluminum hydride, alane, triethoxysilane and phenylsilane.

The process of the invention opens up an economical route to optically active chiral bisphosphinylalkanes of the formula (I), in which the reaction can be carried out simply in all four steps and inexpensive starting materials (which can be used in the form of racemic diastereomer mixtures) and reagents are used. Since reaction conditions which are problematical in process engineering terms, for example large number of steps, low temperatures or aggressive reagents are avoided, the process of the invention is particularly suitable for use on an industrial scale.

The optically active chiral bisphosphinylalkanes of the formula (I) which can be obtained by the process of the invention are suitable for use as ligands for organic metal catalysts, especially organic transition metal catalysts, for asymmetric synthesis. They are especially suitable for preparing chiral transition metal catalysts for asymmetric hydrogenations, hydroformylations, hydroborations and allylic alkylations as described, for example, in Catalytic Asymmetric Synthesis, Wiley-VCH 2000, I. Ojima (Editor).

The present invention accordingly also provides a process for preparing optically active transition metal catalysts by preparing an optically active chiral bisphosphinylalkane of the formula (I) by the above-described process and subsequently bringing the bisphosphinylalkane of the formula (I) prepared in this way into contact with a suitable transition metal compound. For this purpose, suitable transition metals, for example Fe, Ru, Os, Co, Rh, Ir, Ni, Pd, Pt, Cu, Ag or Au, advantageously in the form of compounds which are soluble in the reaction medium selected, for example salts or complexes with suitable ligands such as carbonyl, acetylacetonate, hydroxy, cyclooctadiene, norbornadiene, cyclooctene, methoxy, benzene, thymol, halide such as chloride, bromide or iodide, acetyl or other aliphatic or aromatic carboxylates, are brought into contact with the chiral bisphosphinylalkane of the formula (I) prepared according to the invention. Transition metal compounds which are preferred for the purposes of the process of the invention are, for example, Rh(I), Rh(II) and Rh(III) and also Rh(O) compounds, Ir(I), Ir(II), Ir(III), Ir(IV) and Ir(O) compounds, Ru(II), Ru(III), Ru(IV) and Ru(O) compounds, Pd(II), Pd(IV) and Pd(O) compounds and Pt(II), Pt(IV) and Pt(O) compounds, Cu(I), Cu(II), Cu(III) compounds, Ag(I) or Ag(III) compounds, Au(I) or Au(III) compounds, for example in the form of: $Ru(cod)methallyl_2$, $Ru(cod)allyl_2$, $[Ru(benzene)Cl]_2$, $[Ru(thymol)Cl]_2$, $[Ru(thymol)I]_2$, $RhCl_3$, $Rh(OAc)_3$, $[Rh(cod)Cl]_2$, $Rh(CO)_2acac$, $[Rh(cod)OH]_2$, $[Rh(cod)OMe]_2$, $[Rh(cod)_2]BF_4$, $[Rh(cod)_2]PF_6$, $[Rh(cod)_2]OTf$, $[Rh(cod)_2]SbF_6$, $[Rh(nbd)Cl]_2$, $[Rh(nbd)OH]_2$, $[Rh(nbd)OMe]_2$, $[Rh(nbd)_2]BF_4$, $[Rh(nbd)_2]PF_6$, $[Rh(nbd)_2]OTf$, $[Rh(nbd)_2]SbF_6$, $Rh_4(CO)_{12}$, $Rh_6(CO)_{16}$ or $Ir_4(CO)_{12}$, $[Ir(cod)Cl]_2$, $[Ir(cod)_2]BF_4$, $[Ir(nbd)Cl]_2$, $[Ir(nbd)_2]BF_4$, $Pd(OAc)_2$, $Pd(OC(O)CF)_3$, $[Pd(allyl)Cl]_2$, $Pd(dba)_2$, $Pd_2(dba)_3CHCl_3$, $PdCl_2$, $PtCl_2$, $[Pt(cod)_2]OTf_2$, $[Pt(cod)_2](BF_4)_2$, $[Pt(nbd)_2]OTf_2$, $[Pt(nbd)_2](BF_4)_2$, $CuOTf$, $AgOTf$, $AuCl_3$, where "acac" is an acetylacetonate ligand, "dba" is dibenzylideneacetone, "cod" is a 1,5-cyclooctadiene ligand and "nbd" is a norbornadiene ligand and "Tf" is triflate.

The transition metal compounds mentioned and the optically active chiral bisphosphinylalkane of the formula (I) prepared according to the invention can be brought into contact with one another in a manner known to those skilled in the art, as described, for example, in Transition Metals for Organic Synthesis, Wiley-VCH 1998, M. Beller, C. Bolm (Editors). The chiral transition metal catalysts which are obtainable in this way can be isolated and used further or can be formed in situ in a reaction to be catalyzed.

The abovementioned and further suitable transition metal compounds and complexes are known and adequately described in the literature or can be prepared by a person skilled in the art using methods analogous to those for the known compounds.

In a particularly preferred embodiment, the process of the invention is suitable for preparing optically active transition metal catalysts for the asymmetric hydrogenation of citral, i.e. of mixtures of geranial and neral to form optically active citronellal. The present invention accordingly also provides a process for preparing optically active citronellal, preferably D-citronellal, by asymmetric hydrogenation of citral or geranial and/or neral in the presence of an optically active transition metal catalyst prepared as described above. In this context, preferred chiral transition metal catalysts are ones which can be prepared by bringing an optically active chiral bisphosphinylalkane of one of the formulae (1) to (7) prepared in accordance with the process of the invention into contact with one of the preferred transition metal compounds mentioned above, in particular $Rh(CO)_2acac$, $[Rh(cod)OH]_2$, $[Rh(cod)OMe]_2$, $Rh_4(CO)_{12}$, $Rh_6(CO)_{16}$ or $Ir_4(CO)_{12}$. A particularly preferred chiral transition metal catalyst for the purposes of this aspect of the present invention is R,R-chiraphos of the formula (I).

The optically active citronellal which can be obtained in this way is a valuable fragrance and a valuable intermediate for producing higher value-added products. In particular, optically active citronellal is useful for preparing optically active isopulegol by intramolecular cyclization. Optically active menthol can be prepared by hydrogenation of optically active isopulegol.

EXAMPLES

The following examples serve to illustrate the invention without restricting it in any way:

The diastereomeric purity of the reaction products described was determined by gas-chromatographic analysis under the following conditions: analytical method: gas chromatography; column: OV-1 Macherey & Nagel, 25 m (Examples 1 and 2) or 10 m; temperature program: 50° C., 5 min (Example 1) or 2 min; 20° C./min, 300° C.).

Example 1

Preparation of 4,5-dimethyl-[1,3,2]dioxathiolane 2,2-dioxide 0.88 mol (105 g) of thionyl chloride was added dropwise at room temperature to a solution of 0.44 mol (40 g) of 2,3-dihydroxybutane (cis/trans mixture) in 200 ml of $CH_2Cl_2$ over a period of 3 hours while cooling and stirring vigorously. The HCl gas formed was passed through a wash bottle filled with NaOH solution to neutralize it. After the addition was complete, the reaction mixture was stirred under reflux for 1 hour. The solvent was removed under reduced pressure and the residue was immediately used for the further reaction.

1300 ml of sulfuric acid (10%) were added at 0° C. to a solution of 0.37 mol (50.7 g) of 4,5-dimethyl-[1,3,2]dioxathiolane 2-oxide in 400 ml of $CH_2Cl_2$. While stirring vigorously, 0.42 mol (66 g) of $KMnO_4$ was added in small portions in such a way that the internal temperature remained below 10° C. The addition was complete when the violet color remained for at least 5 minutes. After heating for 1 hour under reflux, the mixture was cooled to room temperature and the reaction was stopped by addition of sodium bisulfite. The organic phase was separated off, the aqueous phase was extracted 5 times with $CH_2Cl_2$, the combined organic phases were washed until neutral, dried over $MgSO_4$ and evaporated under reduced pressure. This gave 4,5-dimethyl-[1,3,2]dioxathiolane 2,2-dioxide in the form of a brownish liquid (193 mmol, 33 g, 44%) as cis/trans mixture (about 2:1) from which a white solid precipitated after some time.

Example 2

Preparation of hexahydrobenzo[1,3,2]dioxathiol 2,2-dioxide 0.32 mol (38 g) of thionyl chloride was added dropwise at room temperature to a solution of 0.16 mol (19 g) of 1,2-dihydroxycyclohexane (cis/trans mixture) in 150 ml of $CH_2Cl_2$ over a period of 3 hours while cooling and stirring vigorously. The HCl gas formed was passed through a wash bottle filled with NaOH solution to neutralize it. After the addition was complete, the reaction mixture was stirred under reflux for 1 hour. The solvent was removed under reduced pressure and the residue (0.15 mol, 24.4 g, 92%) was immediately used for the further reaction.

400 ml of sulfuric acid (10%) were added to a solution of 0.12 mol (19.6 g) of the sulfite obtained in this way in 100 ml of $CH_2Cl_2$ at 0° C. While stirring vigorously, 0.25 mol (40 g) of $KMnO_4$ was added in small portions in such a way that the internal temperature remained below 10° C. The addition was complete when the violet color remained for at least 5 minutes. After heating under reflux for 1 hour, the mixture was cooled to room temperature and the reaction was stopped by addition of sodium bisulfite. The organic phase was separated off, the aqueous phase was extracted 5 times with $CH_2Cl_2$, the combined organic phases were washed until neutral, dried over $MgSO_4$ and evaporated under reduced pressure. This gave hexahydrobenzo[1,3,2]dioxathiol 2,2-dioxide in the form of a colorless liquid (39 mmol, 6.9 g, 32%) as ~2:1 cis/trans mixture.

Example 3

Preparation of Compound (8)

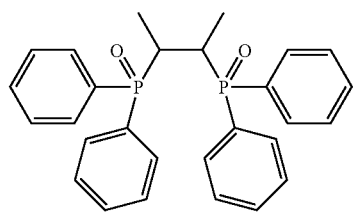

(8)

30 ml of a 50% strength solution of potassium hydroxide in water and 41 mmol (6.25 g) of the reaction product from Example 1 (cis/trans ~2:1) were added in succession to a solution of 121 mmol (24.4 g) of diphenylphosphine oxide in 125 ml of DMSO while stirring and cooling in ice and the mixture was stirred at room temperature for 72 hours. The mixture of cis- and trans-chiraphos dioxide formed initially isomerized virtually completely to the desired trans compound over the reaction time. After the reaction was complete, the mixture was neutralized by addition of 1000 ml of saturated $KHSO_4$ solution, diluted with 300 ml of $CH_2Cl_2$ and the resulting insoluble solid was filtered off. The organic phase was separated off and the aqueous phase was extracted 5 times with a total of 1000 ml of $CH_2Cl_2$. The combined organic phases were completely evaporated at 50° C. under reduced pressure, the residue was washed 3 times with a little pentane and dried under reduced pressure. This gave 40.6 mmol (18.6 g) of slightly yellowish crude product (cis/trans >95:5). Crystallization from Et$_2$O gave 28.1 mmol (12.9 g, 68%) of the compound (8) in the form of a crystalline white solid having a trans content of >98%.

Example 4

Preparation of Compound (9)

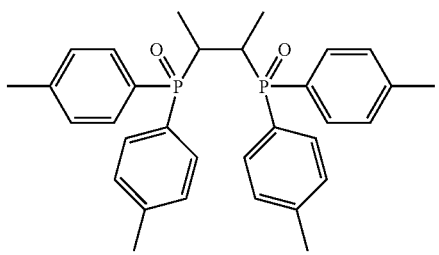

5 ml of a 50% strength KOH solution in water were added to a solution of 19.5 mmol (4.5 g) of di-para-tolylphosphine oxide (J. Gen. Chem. USSR 1992, 62, 1833-1839) in 25 ml of DMSO at 0° C. 7.2 mmol (1.1 g) of the reaction product from Example 1 (cis/trans ~2:1) were added to the now orange solution. The reaction mixture was warmed to room temperature and stirred for a further 72 hours. The reaction was stopped by addition of 1000 ml of saturated KHSO$_4$ solution and 400 ml of CH$_2$Cl$_2$ and removal of insoluble material by filtration. The organic phase is separated off and the aqueous phase is extracted 5 times with CH$_2$Cl$_2$. The combined organic phases were washed until neutral, dried over MgSO$_4$ and evaporated to dryness. The compound (9) was obtained in the form of a yellow foam (5.9 mmol, 3.0 g, 82%, trans content >98%).

Example 5

Preparation of Compound (10)

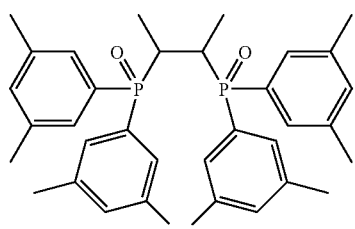

10 ml of a 50% strength KOH solution in water were added to a solution of 38.7 mmol (10.0 g) of bis(3,5-dimethylphenyl)phosphine oxide (org. Lett. 2001, 3, 243-246) in 75 ml of DMSO at 0° C. 14.5 mmol (2.2 g) of the reaction product from Example 1 (cis/trans ~2:1) were added to the now orange solution. The reaction mixture was warmed to room temperature and stirred for a further 18 hours. It was then stirred at 60° C. for 14 hours. The reaction was stopped by addition of 1000 ml of saturated KHSO$_4$ solution and 300 ml of CH$_2$Cl$_2$ and removal of insoluble material by filtration. The organic phase was separated off and the aqueous phase was extracted 5 times with CH$_2$Cl$_2$. The combined organic phases were washed until neutral, dried over MgSO$_4$ and evaporated to dryness. The compound (10) was obtained in the form of a yellow solid (14.4 mmol, 8.2 g, 99%, trans content >98%).

Example 6

Preparation of Compound (11)

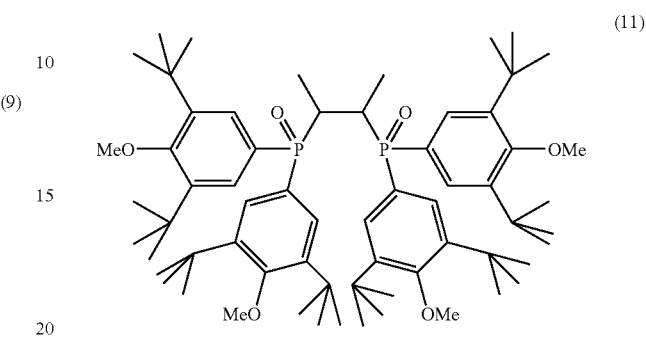

5 ml of a 50% strength KOH solution in water were added to a warm solution of 18.5 mmol (9.0 g) of bis(2,3-di-tert-butyl-4-methoxyphenyl)phosphine oxide (Synth. Catal. 2003, 345, 180-4) in 450 ml of DMSO at 40° C. 7.2 mmol (1.1 g) of the reaction product from Example 1 (cis/trans ~2:1) were added to the now orange solution. The reaction mixture was cooled to room temperature and stirred for a further 24 hours. It was then stirred at 60° C. for 4 hours and subsequently at room temperature for 72 hours. The reaction was stopped by addition of 400 ml of saturated KHSO$_4$ solution and 400 ml of CH$_2$Cl$_2$ and removal of insoluble material by filtration. The organic phase was separated off and the aqueous phase was extracted 5 times with CH$_2$Cl$_2$. The combined organic phases were washed until neutral, dried over MgSO$_4$ and evaporated to dryness. The residue was taken up in 80 ml of MeOH, filtered and evaporated to dryness. The compound (11) was obtained as a white solid after purification by column chromatography on silica gel (MeOH/EtOAc=1:5) and washing with pentane (7.30 mmol, 0.75 g, 11%, trans content >98%).

Example 7

Preparation of Compound (12)

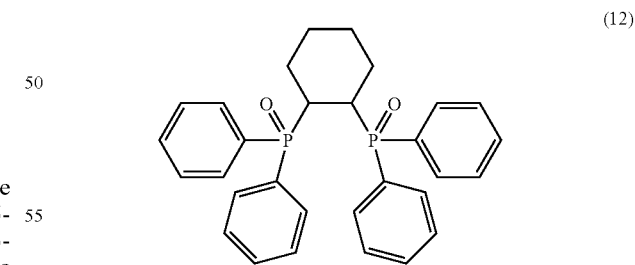

22 ml of a 50% strength KOH solution in water are added to a solution of 84.2 mmol (17.0 g) of diphenylphosphine oxide in 125 ml of DMSO. 28.1 mmol (5.0 g) of the reaction product from Example 2 (cis/trans ~2:1) were added to the now orange solution. The reaction mixture was stirred for a further 96 hours. The reaction was stopped by addition of 500 ml of saturated KHSO$_4$ solution and 300 ml of CH$_2$Cl$_2$ and removal of insoluble material by filtration. The organic phase was separated off and the aqueous phase was extracted 5 times with CH$_2$Cl$_2$. The combined organic phases were washed until neutral, dried over MgSO$_4$ and evaporated to dryness. The compound (12) was obtained as a white solid (20.2 mmol, 9.81 g, 72%, trans content >98%).

Example 8

Resolution of a Racemate

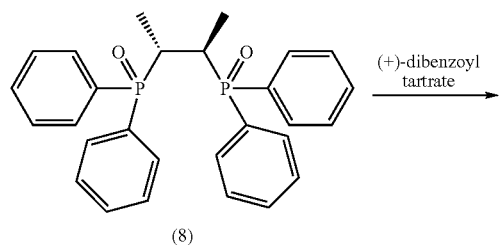

35 mmol (16.1 g) of compound 8 were dissolved in 100 ml of CH$_2$Cl$_2$ under reflux. A boiling solution of 35 mmol (12.54 g) of (+)-dibenzoyl tartrate ((+)-DBT) in 100 ml of EtOAc was introduced into this solution from a second flask by means of a hollow needle. After 2-3 minutes under reflux, the reaction mixture is cooled to room temperature, the solvent is removed under reduced pressure and the residue is taken up 3 times in pentane, with the pentane being distilled off each time. The residue was taken up in 450 ml of EtOAc and heated to reflux. The sparingly soluble adduct of 8 and (+)-DBT was filtered off. The clear solution was evaporated to about 200 ml and further adduct of 8 and (+)-DBT was filtered off. A total of 7.6 mmol (6.23 g) of the adduct were obtained. The solid was dissolved in 100 ml of CH$_2$Cl$_2$ and washed 10 times with 0.1 N NaOH. The organic phase was separated off, dried over MgSO$_4$ and evaporated to dryness. Compound (8*) was obtained in the form of a white solid (9.2 mmol, 4.2 g, 52%).

Example 9

Resolution of a Racemate

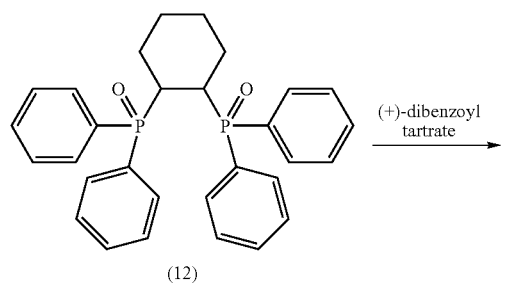

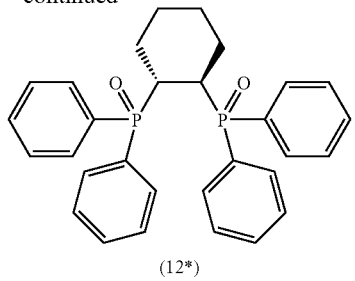

The procedure of Example 3 was repeated using 10.3 mmol (5.0 g) of compound 12, 10.6 mmol (3.8 g) of (+)-DBT, 20 ml of CH$_2$Cl$_2$ and 20 ml of EtOAc to give 1.03 mmol (0.5 g, 20%) of the compound 12*.

Example 10

Resolution of a Racemate

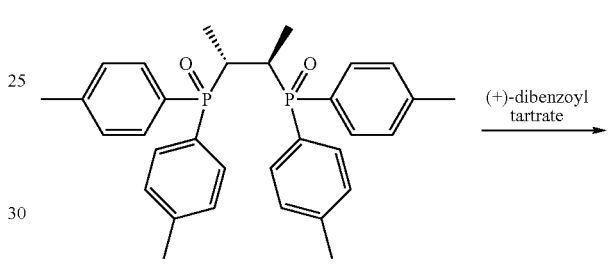

The procedure of Example 8 was repeated using 56 mmol (28.8 g) of the compound (9), 56 mmol (20.1 g) of (+)-DBT, 160 ml of CH$_2$Cl$_2$ and 160 ml of EtOAc to give 23.9 mmol (12.3 g, 43%) of the compound (9*) after triple recrystallization.

Example 11

Reduction

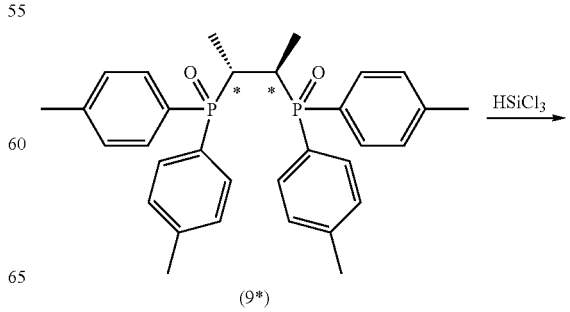

-continued

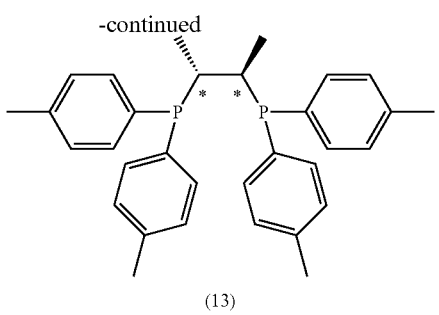

(13)

The procedure described in Matteoli et al. (Tetrahedron: Asymmetry 1997, 8, 1403-1410) was carried out using 22.5 mmol (11.6 g) of the compound (9*) and the product was recrystallized from 100 ml of methanol and subsequently from 200 ml of ethanol to give 17.5 mmol (9.0 g, 79%) of compound (13).

The invention claimed is:

1. A process for preparing an optically active bisphosphinylalkanes of formula (I)

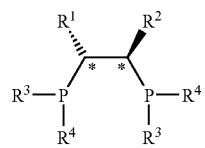

wherein
- $R^1$ and $R^2$
  identically are a straight-chain, branched, or cyclic alkyl radical which has up to 12 carbon atoms and is optionally substituted with one or more identical or different substituents selected from the group consisting of halogen, $C_6$-$C_{12}$-aryl, $NR^5R^6$, $NHR^7$, $OR^8$, and aryl radicals having from 6 to 12 carbon atoms and optionally substituted with one or more identical or different substituents selected from the group consisting of $C_1$-$C_6$-alkyl, halogen, $C_6$-$C_{12}$-aryl, $NR^{5'}R^{6'}$, $NHR^{7'}$, and $OR^{8'}$; or together define an aliphatic ring or bicycle having from 4 to 12 ring members and is optionally substituted with one or more substituents selected from the group consisting of halogen, oxo, $C_6$-$C_{12}$-aryl, $C_1$-$C_{10}$-acyl, and $C_1$-$C_{10}$-sulfonyl, and optionally comprises one or more heteroatoms O or $NR^9$;
- $R^3$ and $R^4$
  identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of $C_1$-$C_{12}$-alkyl, halogen, $NR^{5''}R^{6''}$, $NHR^{7''}$, $OR^{8''}$, sulphonyl, $C(O)OR^{14}$, and $C(O)NR^{14'}R^{14''}$;
- $R^5$, $R^6$, $R^{5'}$, $R^{6'}$, $R^{5''}$, and $R^{6''}$
  are, independently of one another, $C_1$-$C_{12}$-alkyl or $C_6$-$C_{12}$-aryl;
- $R^7$ to $R^{7''}$
  are $C_1$-$C_{10}$-acyl or $C_1$-$C_{10}$-sulfonyl;
- $R^8$ to $R^{8''}$
  are $C_1$-$C_{12}$-alkyl or $C_6$-$C_{12}$-aryl;

- $R^9$ is $C_1$-$C_{12}$-alkyl, $C_6$-$C_{12}$-aryl, $C_1$-$C_{10}$-acyl, or $C_1$-$C_{10}$-sulfonyl;
- $R^{14}$, $R^{14'}$ are hydrogen, $C_1$-$C_{12}$-alkyl, $C_6$-$C_{12}$-aryl, or $C_7$-$C_{17}$-aralkyl;
- $R^{14''}$ is $C_1$-$C_{12}$-alkyl, $C_6$-$C_{12}$-aryl, or $C_7$-$C_{17}$-aralkyl; and
- * is an asymmetrically substituted carbon atom;

comprising a) reacting a diol of formula (II)

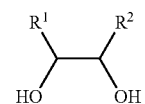

wherein $R^1$ and $R^2$ are as defined in formula (I), to form a compound of formula (III)

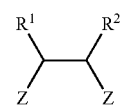

wherein $R^1$ and $R^2$ are as defined in formula (I), and both Z together in formula (III) form a structural fragment selected from group consisting of —O—S(O)$_2$—O—, —O—P(O)(OR$^{15}$)$_2$—O—, —O—C(O)—O—, and —O—C(O)—C(O)—O—, wherein $R^{15}$ is $C_1$-$C_{12}$-alkyl, $C_7$-$C_{17}$-aralkyl, or $C_6$-$C_{12}$-aryl;

b) reacting the compound of formula (III) obtained in a) with a phosphine oxide of formula (IV)

wherein $R^3$ and $R^4$ are as defined in formula (I), in the presence of a base which is capable of deprotonating said phosphine oxide of formula (IV), to form a racemic 1,2-trans-configured-bis(phosphine oxide) of formula (V)

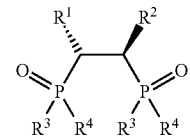

wherein $R^1$, $R^2$, $R^3$, and $R^4$ are as defined in formula (I);

c) resolving the racemic-bis(phosphine oxide) of formula (V) obtained in b) to give an optically active-bis(phosphine oxide) of formula (V*)

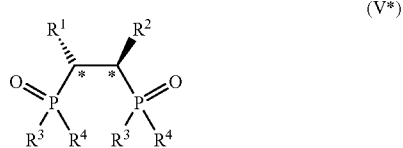

(V*)

wherein $R^1$, $R^2$, $R^3$, and $R^4$ are as defined in formula (I), and

* is an asymmetrically substituted carbon atom, and d) reducing the compound of formula (V*) obtained in c) to give the compound of formula (I).

2. The process of claim 1, wherein
$R^1$ and $R^2$
are, identical and are each a straight-chain, branched, or cyclic alkyl radical having up to 12 carbon atoms or together define an aliphatic ring or bicycle which has from 4 to 12 ring members and is optionally substituted with one or more substituents selected from the group consisting of halogen, oxo, $C_6$-$C_{12}$-aryl, $C_1$-$C_{10}$-acyl, and $C_1$-$C_{10}$-sulfonyl, and optionally comprises one or more heteroatoms O or $NR^9$; and
$R^3$ and $R^4$
are, identically or differently, an aryl radical having from 6 to 12 carbon atoms and is optionally substituted with one or more identical or different substituents selected from the group consisting of $C_1$-$C_6$-alkyl, halogen, $NR^{5''}R^{6''}$, $NHR^{7'}$, $OR^{8''}$, carboxy, and sulphonyl.

3. The process of claim 1, wherein
$R^1$ and $R^2$
are identical and are each a straight-chain, branched, or cyclic alkyl radical having up to 6 carbon atoms or together form an aliphatic ring or bicycle having from 4 to 12 ring members and is optionally substituted with one or more substituents selected from the group consisting of halogen, oxo, $C_6$-$C_{12}$-aryl, $C_1$-$C_{10}$-acyl, and $C_1$-$C_{10}$-sulfonyl, and optionally comprises one or more heteroatoms O or $NR^9$; and
$R^3$ and $R^4$
are identical and are each an aryl radical having from 6 to 12 carbon atoms and is optionally substituted with one or more identical or different substituents selected from the group consisting of $C_1$-$C_{12}$-alkyl, halogen, $NR^{5''}R^{6''}$, $NHR^{7'}$, $OR^{8''}$, carboxy, and sulphonyl.

4. The process of claim 1, wherein $R^1$ and $R^2$ together define a cyclohexyl ring and $R^3$ and $R^4$ are each substituted or unsubstituted phenyl.

5. The process of claim 1, wherein $R^1$ and $R^2$ are each methyl and $R^3$ and $R^4$ are each substituted or unsubstituted phenyl.

6. The process of claim 1, wherein b) is carried out in the presence of a polar aprotic solvent.

7. The process of claim 1, wherein c) is achieved by carrying out a crystallization in the presence of a chiral auxiliary reagent.

8. The process of claim 7, wherein said chiral auxiliary reagent is a chiral carboxylic or sulfonic acid in optically active form.

9. A process for preparing an optically active transition metal catalyst comprising preparing an optically active chiral bisphosphinylalkane of formula (I) by the process of claim 1

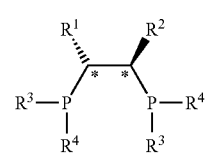

(I)

wherein
$R^1$ and $R^2$
identically are a straight-chain, branched, or cyclic alkyl radical which has up to 12 carbon atoms and is optionally substituted with one or more identical or different substituents selected from the group consisting of halogen, $C_6$-$C_{12}$-aryl, $NR^5R^6$, $NHR^7$, $OR^8$, and aryl radicals having from 6 to 12 carbon atoms and optionally substituted with one or more identical or different substituents selected from the group consisting of $C_1$-$C_6$-alkyl, halogen, $C_6$-$C_{12}$-aryl, $NR^{5'}R^{6'}$, $NHR^{7'}$, and $OR^{8'}$; or together define an aliphatic ring or bicycle having from 4 to 12 ring members and is optionally substituted with one or more substituents selected from the group consisting of halogen, oxo, $C_6$-$C_{12}$-aryl, $C_1$-$C_{10}$-acyl, and $C_1$-$C_{10}$-sulfonyl, and optionally comprises one or more heteroatoms O or $NR^9$;
$R^3$ and $R^4$
identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of $C_1$-$C_{12}$-alkyl, halogen, $NR^{5''}R^{6''}$, $NHR^{7''}$, $OR^{8''}$, sulphonyl, $C(O)OR^{14}$, and $C(O)NR^{14'}R^{14''}$;
$R^5$, $R^6$, $R^{5'}$, $R^{6'}$, $R^{5''}$, and $R^{6''}$
are, independently of one another, $C_1$-$C_{12}$-alkyl or $C_6$-$C_{12}$-aryl;
$R^7$ to $R^{7''}$
are $C_1$-$C_{10}$-acyl or $C_1$-$C_{10}$-sulfonyl;
$R^8$ to $R^{8''}$
are $C_1$-$C_{12}$-alkyl or $C_6$-$C_{12}$-aryl;
$R^9$ is $C_1$-$C_{12}$-alkyl, $C_6$-$C_{12}$-aryl, $C_1$-$C_{10}$-acyl, or $C_1$-$C_{10}$-sulfonyl;
$R^{14}$, $R^{14'}$
are hydrogen, $C_1$-$C_{12}$-alkyl, $C_6$-$C_{12}$-aryl, or $C_7$-$C_{17}$-aralkyl;
$R^{14''}$ is $C_1$-$C_{12}$-alkyl, $C_6$-$C_{12}$-aryl, or $C_7$-$C_{17}$-aralkyl; and
* is an asymmetrically substituted carbon atom;
and contacting said chiral bisphosphinyl alkane of formula (I) with a suitable transition metal compound.

10. The process of claim 9, wherein said transition metal compound is a compound of a metal selected from the group consisting of Fe, Ru, Co, Rh, Ir, Ni, Pd, Pt, Cu, Ag, and Au.

11. The process of claim 9, wherein said chiral bisphosphinylalkane is (R,R)-chiraphos.

12. A process for preparing an optically active bisphosphinylalkane of formula (I)

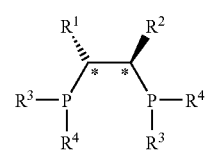

(I)

wherein

R$^1$ and R$^2$
  identically are a straight-chain, branched, or cyclic alkyl radical which has up to 12 carbon atoms and is optionally substituted with one or more identical or different substituents selected from the group consisting of halogen, C$_6$-C$_{12}$-aryl, NR$^5$R$^6$, NHR$^7$, OR$^8$, and aryl radicals having from 6 to 12 carbon atoms and optionally substituted with one or more identical or different substituents selected from the group consisting of C$_1$-C$_6$-alkyl, halogen, C$_6$-C$_{12}$-aryl, NR$^{5'}$R$^{6'}$, NHR$^{7'}$, and OR$^{8'}$; or together define an aliphatic ring or bicycle having from 4 to 12 ring members and is optionally substituted with one or more substituents selected from the group consisting of halogen, oxo, C$_6$-C$_{12}$-aryl, C$_1$-C$_{10}$-acyl, and C$_1$-C$_{10}$-sulfonyl, and optionally comprises one or more heteroatoms O or NR$^9$;

R$^3$ and R$^4$
  identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of C$_1$-C$_{12}$-alkyl, halogen, NR$^{5''}$R$^{6''}$, NHR$^{7''}$, OR$^{8''}$, sulphonyl, C(O)OR$^{14}$, and C(O)NR$^{14'}$R$^{14''}$;

R$^5$, R$^6$, R$^{5'}$, R$^{6'}$, R$^{5''}$, and R$^{6''}$
  are, independently of one another, C$_1$-C$_{12}$-alkyl or C$_6$-C$_{12}$-aryl;

R$^7$ to R$^{7''}$
  are C$_1$-C$_{10}$-acyl or C$_1$-C$_{10}$-sulfonyl;

R$^8$ to R$^{8''}$
  are C$_1$-C$_{12}$-alkyl or C$_6$-C$_{12}$-aryl;

R$^9$ is C$_1$-C$_{12}$-alkyl, C$_6$-C$_{12}$-aryl, C$_1$-C$_{10}$-acyl, or C$_1$-C$_{10}$-sulfonyl;

R$^{14}$, R$^{14'}$ are hydrogen, C$_1$-C$_{12}$-alkyl, C$_6$-C$_{12}$-aryl, or C$_7$-C$_{17}$-aralkyl;

R$^{14''}$ is C$_1$-C$_{12}$-alkyl, C$_6$-C$_{12}$-aryl, or C$_7$-C$_{17}$-aralkyl; and

* is an asymmetrically substituted carbon atom;

comprising a) reacting a diol of formula (II)

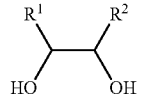

(II)

wherein R$^1$ and R$^2$ are as defined in formula (I), to form a compound of formula (III)

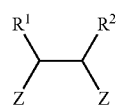

(III)

wherein R$^1$ and R$^2$ are as defined in formula (I), and both Z together in formula (III) form a structural fragment selected from the group consisting of —O—S(O)$_2$—O—, —O—P(O)(OR$^{15}$)$_2$—O—, —O—C(O)—O—, and —O—C(O)—C(O)—O—, wherein R$^{15}$ is C$_1$-C$_{12}$-alkyl, C$_7$-C$_{17}$-aralkyl, or C$_6$-C$_{12}$-aryl;

b) reacting the compound of formula (III) obtained in a) with a phosphine oxide of formula (IV)

(IV)

wherein R$^3$ and R$^4$ are as defined in formula (I), in the presence of a base-selected from the group consisting of alkali metal hydroxides, alkaline earth metal hydroxides, alkali metal alkoxides, and alkaline earth metal alkoxides, to form a racemic 1,2-trans-configured-bis(phosphine oxide) of formula (V)

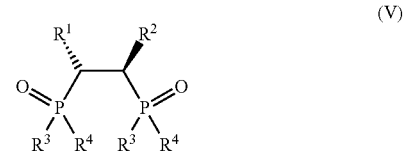

(V)

wherein R$^1$, R$^2$, R$^3$, and R$^4$ are as defined in formula (I);

c) resolving the racemic bis(phosphine oxide) of formula (V) obtained in b) to give an optically active bis(phosphine oxide) of formula (V*)

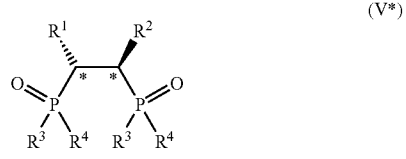

(V*)

wherein R$^1$, R$^2$, R$^3$, and R$^4$ are as defined in formula (I), and

* is an asymmetrically substituted carbon atom, and d) reducing the compound of formula (V*) obtained in c) to give the compound of formula (I).

13. The process of claim 1, wherein R$^3$ and R$^4$ identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of C$_1$-C$_{12}$-alkyl, halogen, NR$^{5''}$R$^{6''}$, NHR$^{7''}$, OR$^{8''}$, sulphonyl, and C(O)NR$^{14'}$R$^{14''}$.

14. The process of claim 12, wherein R$^3$ and R$^4$ identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of C$_1$-C$_{12}$-alkyl, halogen, NR$^{5''}$R$^{6''}$, OR$^{8''}$, sulphonyl, and C(O)NR$^{14'}$R$^{14''}$.

15. The process of claim 1, wherein R$^3$ and R$^4$ identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of $C_1$-$C_{12}$-alkyl, halogen, $NR^{5"}R^{6"}$, $NHR^{7"}$, $OR^{8"}$, sulphonyl and $C(O)NR^{14'}R^{14"}$.

16. The process of claim 12, wherein $R^3$ and $R^4$ identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of $C_1$-$C_{12}$-alkyl, halogen, $NR^{5"}R^{6"}$ $NHR^{7"}$, $OR^{8"}$, sulphonyl, and $C(O)NR^{14'}R^{14"}$.

17. A process for preparing an optically active bisphosphinylalkane of formula (I)

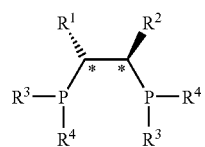

(I)

wherein $R^1$ and $R^2$ together define a cyclohexyl ring;

$R^3$ and $R^4$ identically or differently are each a straight-chain, branched, or cyclic alkyl radical having up to 12 carbon atoms or an aryl radical having from 6 to 12 carbon atoms, each of which is optionally substituted with one or more identical or different substituents selected from the group consisting of $C_1$-$C_{12}$-alkyl, halogen, $NR^{5"}R^{6"}$, $NHR^{7"}$, $OR^{8"}$, sulphonyl, $C(O)OR^{14}$, and $C(O)NR^{14'}R^{14"}$;

$R^{5"}$ and $R^{6"}$ are, independently of one another, $C_1$-$C_{12}$-alkyl or $C_6$-$C_{12}$-aryl;

$R^{7"}$ is $C_1$-$C_{10}$-acyl or $C_1$-$C_{10}$-sulfonyl;

$R^{8"}$ is $C_1$-$C_{12}$-alkyl or $C_6$-$C_{12}$-aryl;

$R^{14}$ and $R^{14'}$ are hydrogen, $C_1$-$C_{12}$-alkyl, $C_6$-$C_{12}$-aryl, or $C_7$-$C_{17}$-aralkyl;

$R^{14"}$ is $C_1$-$C_{12}$-alkyl, $C_6$-$C_{12}$-aryl, or $C_7$-$C_{17}$-aralkyl; and

* is an asymmetrically substituted carbon atom;

comprising a) reacting a diol of formula (II)

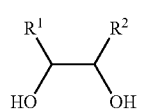

(II)

wherein $R^1$ and $R^2$ are as defined in formula (I), to form a compound of formula (III)

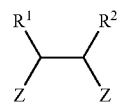

(III)

wherein $R^1$ and $R^2$ are as defined in formula (I), and each Z is a leaving group or both Z together form a structural fragment selected from the group consisting of —O—S$(O)_2$—O—, —O—P(O)(OR$^{15}$)$_2$—O—, —O—C(O)—O—, and —O—C(O)—C(O)—O—, wherein $R^{15}$ is $C_1$-$C_{12}$-alkyl, $C_7$-$C_{17}$-aralkyl, or $C_6$-$C_{12}$-aryl;

b) reacting the compound of the formula (III) obtained in a) with a phosphine oxide of formula (IV)

(IV)

wherein $R^3$ and $R^4$ are as defined in formula (I), in the presence of a base which is capable of deprotonating said phosphine oxide of formula (IV), to form a racemic 1,2-trans-configured bis(phosphine oxide) of formula (V)

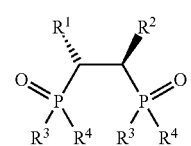

(V)

wherein $R^1$, $R^2$, $R^3$, and $R^4$ are as defined in formula (I);

c) resolving the racemic bis(phosphine oxide) of formula (V) obtained in b) to give an optically active bis(phosphine oxide) of formula (V*)

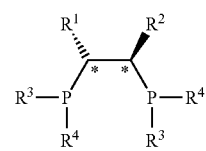

(I)

wherein $R^1$, $R^2$, $R^3$, and $R^4$ are as defined in formula (I), and

* is an asymmetrically substituted carbon atom, and d) reducing the compound of the formula (V*) obtained in c) to give the compound of formula (I).

18. The process of claim 17, wherein $R^3$ and $R^4$ are each substituted or unsubstituted phenyl.

* * * * *